(12) United States Patent
Riedel et al.

(10) Patent No.: US 6,864,387 B2
(45) Date of Patent: Mar. 8, 2005

(54) PROCESS FOR PREPARING SULFONATED ARYLPHOSPHINES

(75) Inventors: Michael Riedel, Bay City, TX (US); Ernst Wiebus, Oberhausen (DE); Carl D Frohning, Wesel (DE); Wilfried Fenske, Hamminkeln (DE); Florian Rampf, Burghausen (DE); Jurgen Herwig, Hunxe (DE); Helmut Bahrmann, Hamminkeln (DE); Klaus Bergrath, Oberhausen (DE); Wolfgang Zgorzel-Ski, Oberhausen (DE); Robert Eckl, Munich (DE); Hans Bohnen, Moers (DE); Richard Fischer, Oberhausen (DE); Kurt Schalapski, Oberhausen (DE); Wolfgang Greb, Dinslaken (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/413,014

(22) Filed: Apr. 14, 2003

(65) Prior Publication Data

US 2004/0019236 A1 Jan. 29, 2004

Related U.S. Application Data

(62) Division of application No. 09/937,640, filed as application No. PCT/EP00/03241 on Apr. 12, 2000, now Pat. No. 6,610,881.

(30) Foreign Application Priority Data

Apr. 22, 1999 (DE) .......................................... 199 18 284
Feb. 18, 2000 (DE) .......................................... 100 07 341

(51) Int. Cl.$^7$ ............................................ C07C 304/00
(52) U.S. Cl. ............................... 562/35; 562/30; 568/13
(58) Field of Search ......................... 562/30, 35; 568/13

(56) References Cited

U.S. PATENT DOCUMENTS

| | | | | |
|---|---|---|---|---|
| 4,710,321 A | * | 12/1987 | Bahrmann et al. | ............ 562/35 |
| 5,274,183 A | * | 12/1993 | Herrman et al. | ............... 562/35 |
| 5,347,045 A | * | 9/1994 | Herrmann et al. | ............ 562/35 |
| 5,684,182 A | * | 11/1997 | Naumann et al. | ............. 562/35 |
| 5,847,200 A | * | 12/1998 | Bahrmann et al. | ............ 562/35 |
| 5,925,785 A | * | 7/1999 | Stelzer et al. | .................. 562/35 |
| 6,613,939 B2 | * | 9/2003 | Aouni et al. | ................... 562/35 |

OTHER PUBLICATIONS

CA:69:86252 abs of Industrial and Engineering Chemistry Product Research and Devel. by Tucci, Raymond 7(3) pp 227–8, 1968.*
CA:108::211031 abs of Journal of Molecular Catalysis by Larpent et al 44(2) pp 191–5 1988.*

* cited by examiner

Primary Examiner—Johann R. Richter
Assistant Examiner—Karl Puttlitz
(74) Attorney, Agent, or Firm—Muserlian, Lucas and Mercanti

(57) ABSTRACT

A process for preparing solutions of sulfonated arylphosphines comprising reacting arylphosphines with oleum, diluting the sulfonation mixture with water, extracting the diluted sulfonation mixture with a solution of a water-insoluble organic solvent, reacting the organic phase with a solution of an inorganic base in water, adjusting the resulting aqueous solutin of sulfonated arylphosphines to a pH of up to 3 by addition of an acid, and passing an inert gas stream through the aqueous solution comprising sulfonated arylphosphines until sulfur is no longer liberated from the aqueous solution of sulfonated arylphosphines.

11 Claims, No Drawings

PROCESS FOR PREPARING SULFONATED ARYLPHOSPHINES

PRIOR APPLICATION

This application is a division of U.S. patent application Ser. No. 09/937,640 filed Dec. 12, 2001, now U.S. Pat. No. 6,610,881 which is a 371 of PCT/EP00/03241 filed Apr. 12, 2000.

The present invention relates to a process for reducing the sulfur dioxide or sulfite content of solutions of sulfonated arylphosphines, in particular of aqueous solutions of sulfonated arylphosphines.

Complexes which contain a metal of group VIII of the Periodic Table of the Elements as central atom and phosphorus(III) compounds such as phosphines as ligands and in addition possibly further groups capable of complex formation have gained increasing importance as catalysts in recent years. Thus, the industrially widely practiced reaction of olefins with synthesis gas (mixture of hydrogen and carbon monoxide) to give aldehydes (hydroformylation) is carried out in the presence of catalysts made up of cobalt or rhodium and triphenylphosphine. Due to the solubility of these catalysts in organic solvents, the reaction proceeds in a homogeneous phase.

However, instead of in a homogeneous phase, the hydroformylation can also be carried out in heterogeneous reaction systems. The use of catalysts dissolved in water frequently has the particular advantage that these catalysts can be separated simply and gently from the reaction products which are sparingly soluble or insoluble in water and the catalysts can be returned to the reactor.

The use of rhodium-containing aqueous solutions of sulfonated arylphosphines as aqueous catalyst solution for the preparation of aldehydes by reaction of olefins with carbon monoxide and hydrogen (hydroformylation) is known. Such a process is described in DE-A-26 27 354. The rhodium-containing aqueous solution contains, for example, tris(m-sulfophenylphosphine) (TPPTS) as ligand. The use of catalysts dissolved in water has the particular advantage that these catalysts can be separated simply and gently from the reaction products which are sparingly soluble or insoluble in water by means of simple phase separation and can be returned to the reactor. A hydroformylation process carried out in this way is also referred to as a two-phase hydroformylation process.

Sulfonated phenylphosphines are obtained by a process described in J. Chem. Soc. (1985), pp. 281 and 282, by reaction of triphenylphosphine with oleum. In this process, the reaction mixture is firstly heated on a water bath and then hydrolyzed with water. Subsequent neutralization with NaOH forms the corresponding sodium salts of the sulfonated triphenylphosphine.

In the reaction of arylphosphines with a solution of sulfur trioxide in concentrated sulfuric acid, generally referred to as oleum or as "fuming sulfuric acid", sulfite salts are also formed in small amounts in addition to the desired sulfonated arylphosphines. Furthermore, the reaction solution contains some dissolved sulfur dioxide. In addition, sulfite or sulfur dioxide react further with the sulfonated arylphosphine to form the corresponding phosphine sulfide. In the following, the term sulfite refers to the sulfite or hydrogensulfite anion of sulfurous acid. As is known, sulfur dioxide is present in aqueous solution in physically dissolved form but also reacts with water to form sulfurous acid which is converted by proton abstraction into the hydrogensulfite or sulfite anion.

A serious disadvantage of the known process for preparing sulfonated arylphosphines is the undesirable formation of phosphorus-oxygen compounds which are formed by oxidation of trivalent phosphorus to pentavalent phosphorus by $SO_3$ dissolved in the oleum. This redox reaction can be reduced in accordance with the teachings of EP-A-0 632 047 by addition of boric acid to the reaction mixture, but in the known process this results in formation of considerable amounts of boron compounds which have to be removed again from the reaction products, which is costly.

In the redox reaction of sulfur trioxide with the phosphine used, sulfur dioxide is formed as reduction product of the sulfur trioxide and the corresponding phosphine oxide is formed from the phosphine. This sulfur dioxide is not removed in the work-up of the reaction mixture with aqueous sodium hydroxide solution as disclosed, for example, in EP-A-0 632 047. Sodium sulfite therefore remains as impurity in the solution of the sulfonated arylphosphine. It is assumed that this sodium sulfite is the source and cause of the contamination of aldehydes with sulfur compounds in the two-phase hydroformylation and that these sulfur compounds are responsible for the poisoning of hydrogenation catalysts in the subsequent hydrogenation of the aldehydes to give alcohols.

It is known that inorganic and organic sulfur compounds, (e.g. butanethiol or thiobutyl butyrate) which are formed in the reaction of the aldehydes formed during the hydroformylation reaction and their downstream products, for example alcohols, with sulfur dioxide or sulfite are responsible for the poisoning of hydrogenation catalysts used for the subsequent hydrogenation of the aldehydes to give the oxo alcohols. Furthermore, the sulfur-containing compounds formed persistently and, in particular, disadvantageously interfere in various chemical reactions and lead, for example, to the formation of undesirable mixed aldols or trimerization products from the aldehydes.

It is therefore an object of the invention to develop a simple process by means of which sulfonated arylphosphines, for example TPPTS, can be prepared reliably and free of sodium sulfite.

This object is achieved by a process of the generic type mentioned at the outset, in which, after reaction of the arylphosphines with oleum, the sulfonation mixture is firstly diluted with water and cooled, an inert gas stream is then passed through the diluted sulfonation mixture until $SO_2$ is no longer liberated from the diluted sulfonation mixture and the latter is then worked up further in a customary manner.

It has surprisingly been found that as a result of the process of the invention interfering sulfur compounds are no longer detectable in the aldehydes produced by the two-phase hydroformylation. It is particularly surprising that the small amount of sodium sulfite formed sulfur compounds which function as catalyst poisons. They therefore do not come from the sulfur-containing sulfonic acid groups of the sulfonated arylphosphines. If the hydroformylation is carried out using arylphosphines sulfonated by the process of the invention, it is possible to increase the life of hydrogenation catalysts, for example in the hydrogenation of 2-ethylhexenal to 2-ethylhexanol, by a factor of two or more. This lengthening of the life of hydrogenation catalysts results in a considerable economic advantage in the preparation of industrial alcohols.

According to the invention, the sulfonation is carried out in accordance with the teachings of DE-A-26 27 354. After dilution of the sulfonation mixture of arylphosphines and oleum with water to a sulfuric acid content of from 25 to 30% and immediate cooling, an inert gas stream is passed through the diluted sulfonation mixture. The treatment with the gas can be carried out batchwise or continuously.

The amount of inert gas per kg of diluted sulfonation mixture and the time of the treatment with gas depend on the geometry of the gas treatment apparatus. In general, the conditions and the geometry are to be selected so that the diluted sulfonation mixture is largely freed of $SO_2$ present (at least 90%). In a continuous treatment with gas, for example in a packed column, a mean gas treatment time of from 2 to 100 minutes, preferably from 2 to 20 minutes, is useful. In a continuous gas treatment apparatus, a total amount in the range from 5 to 500 l of inert gas, preferably from 10 to 200 l, particularly preferably from 20 to 100 l, are required per kg of diluted sulfonation mixture.

The further work-up of the diluted and purified sulfonation mixture is carried out in a known manner in accordance with the teachings of EP-A-0 632 047.

Thus, the diluted sulfonation mixture is extracted with the solution of a water-insoluble amine, for example triisooctylamine, in a water-insoluble organic solvent, for example toluene, to remove the sodium sulfate. Subsequently, the organic phase obtained is reacted with the solution of an inorganic base in water. The base is used here in an amount equivalent to the amount of dissolved amine salt. Excess base is to be avoided because it contaminates the end product. In this way, an aqueous solution of the sulfonated arylphosphine is obtained with recovery of the water-insoluble amine. The amine is again available for reuse. The conversion of the sulfonated phosphines into the aqueous phase is also referred to as reextraction. Preference is given to preparing an aqueous solution of tris(m-sulfophenyl)phosphine trisodium salt (abbreviated as TPPTS) in this way. After addition of rhodium to the aqueous TPPTS solution, either in the form of metallic rhodium or in the form of rhodium compounds, the aqueous solution is used as catalyst solution.

In this embodiment of the process of the invention, the sulfur dioxide formed can only be removed during the preparation of the sulfonated arylphosphines. This embodiment does not allow the sulfur dioxide to be removed from the finished aqueous solution which is obtained after extraction with the water-insoluble amine and reextraction with the inorganic base and contains the water-soluble ligand. This disadvantage could only be overcome by modification of the existing production plant for preparing the sulfonated arylphosphines. The modification of the existing production plant for preparing sulfonated arylphosphines, could, however, be circumvented if the degassing step were applied to the finished solution of sulfonated arylphosphines leaving the production plant. Furthermore, the above-described embodiment of the process of the invention does not make it possible to remove the sulfite from solutions of sulfonated arylphosphines which contain sulfite in addition to sulfur dioxide.

A further object of the invention is therefore a process for preparing solutions of sulfonated arylphosphines which have a very low content of by-products, in particular sulfite, sulfur dioxide and phosphine sulfide, which process can be applied to finished solutions comprising the water-soluble ligand and can be installed without problems in an existing production plant for the preparation of sulfonated arylphosphines. The solutions comprising the water-soluble ligand obtained in this way should, after addition of rhodium as metal or as compound, be able to be used directly in the process disclosed in DE-A-26 27 354 for preparing aldehydes from olefins in the presence of an aqueous catalyst solution by the two-phase method.

The invention therefore likewise provides a process for preparing solutions of sulfonated arylphosphines obtained by reaction of arylphosphines with oleum and dilution of the sulfonation mixture with water, extraction of the diluted sulfonation mixture with the solution of a water-insoluble amine in a water-insoluble organic solvent, reaction of the organic phase with the solution of an inorganic base in water, wherein the resulting aqueous solution comprising sulfonated arylphosphines is brought to a pH of up to 3 by addition of an acid, and an inert gas stream is then passed through the aqueous solution comprising sulfonated arylphosphines until sulfur dioxide is no longer liberated from the aqueous solution comprising sulfonated arylphosphines.

It has now surprisingly been found that even sulfite-containing solutions of sulfonated arylphosphines, for example those obtained by the process known from EP-A-0 632 047, can be freed of the sulfite again without problems. Surprisingly, it was discovered that during the preparation process the sulfonated arylphosphines react only slowly with sulfite to form the phosphine sulfides and phosphine oxides containing pentavalent phosphorus. Only after addition of rhodium as metal or as a compound to the aqueous solution and pressurization with synthesis gas, i.e. a mixture of hydrogen and carbon monoxide, at elevated pressure and elevated temperature are damaging sulfur-containing compounds formed by reaction with the sulfite present. The formation of damaging sulfur-containing compounds can, however, be suppressed if the freshly prepared aqueous solution of the sulfonated arylphosphines is treated by the process of the invention and only then is rhodium added and a synthesis gas injected at elevated temperature. If synthesis gas is injected first, this is referred to as preformation of the catalyst. The preformation step is followed by addition of olefin and reaction to give the desired aldehydes. Of course, it is also possible for the fresh aqueous solution of sulfonated arylphosphines treated according to the invention to be used, after addition of rhodium, directly in the hydroformylation process which proceeds in the presence of synthesis gas and an olefinic compound.

The process of the invention makes it possible to free fresh aqueous solutions of sulfonated arylphosphines, which have previously not yet been used in the catalysis process, of the sulfite or sulfur dioxide and thus to prevent the formation of damaging sulfur-containing compounds during the subsequent catalysis process.

To carry out this process, it is possible to employ the plant which has been found to be useful for the continuous treatment of the diluted sulfonation mixture with inert gas. However, it is also possible to place the finished solution of sulfonated arylphosphines batchwise in a stirred vessel and, after addition of acid, to pass inert gas through the solution. The implementation of this process therefore requires no expensive enlargement of the production plant. The quality of degassing (removal of sulfite or sulfur dioxide) is comparable with the degassing of the diluted sulfonation mixture. After the fresh aqueous solutions of sulfonated arylphosphines treated according to the invention have been used in the two-phase hydroformylation process, only small amounts of sulfur compounds can be detected in the desired aldehydes. The use of aldehydes which have been prepared in the two-phase hydroformylation process using the aqueous solution of sulfonated arylphosphines treated according to the invention is found to be particularly advantageous in the subsequent hydrogenation to form the corresponding alcohols. The extremely low content of interfering sulfur compounds in the hydrogenation stage considerably increases the life of the hydrogenation catalysts used. Thus, for example, the hydrogenation of 2-ethylhexenal, the reaction product obtained after the aldol condensation of n-butyraldehyde and elimination of water, to 2-ethylhexanol can be made more economical since the life of the hydrogenation catalysts used is increased by a factor of two or more. This lengthening of the operating life of the catalyst results in a considerable economic advantage in the preparation of industrially important alcohols due to a reduced need to replace the catalyst and lower catalyst procurement and disposal costs associated therewith.

The sulfonation is carried out according to the teachings of DE-A-26 27 354. The sulfonation mixture of arylphosphines and oleum is diluted with water to a sulfuric acid content of from 25 to 30% by weight, based on the total mass of the solution, to give the diluted sulfonation mixture. The diluted sulfonation mixture is subsequently worked up as described in EP-A-0 632 047. Thus, the diluted sulfonation mixture is extracted with the solution of a water-insoluble amine, for example triisooctylamine, in a water-insoluble organic solvent, for example toluene, to remove the sodium sulfate. The organic phase obtained is subsequently reacted with the solution of an inorganic base in water. The base is used here in an amount equivalent to the amount of dissolved amine salt. Excess base is to be avoided because it contaminates the end product. In this way, an aqueous solution of the sulfonated arylphosphine is obtained with recovery of the water-insoluble amine. The amine is available again for reuse. The transfer of the sulfonated phosphines into the aqueous phase is also referred to as reextraction. Suitable bases for transferring the sulfonated phosphines into the aqueous phase are the hydroxides of the alkali metals and alkaline earth metals, in particular alkali metal hydroxide, ammonia and also the alkali metal carbonates.

The procedure known from EP-A-0 632 047 for working up the diluted sulfonation mixture is expressly incorporated by reference at this point.

To remove the sulfite, the aqueous solution comprising the sulfonated arylphosphine is, according to the invention, brought to a pH of up to 3, preferably from 0 to 2, by means of an acid. Acids which can be used are inorganic or organic acids, for example sulfuric acid, phosphoric acid, nitric acid, hydrochloric acid or formic acid and acetic acid in concentration form or as solutions having a concentration of from 1 to 98% by weight. Preference is given to using aqueous sulfuric acid having a concentration of from 20 to 60% by weight. It has surprisingly been found that the degassing rates are higher, the lower the pH. It is therefore particularly advantageous to set the pH to a value in the range from 0 to 2 for carrying out the process of the invention. The acid is added at a temperature of from 0° C. to 70° C., preferably from 10° C. to 14° C. Subsequently, an inert gas stream is passed through the solution. The treatment with gas can be carried out batchwise or continuously.

After the gas treatment has been completed, the pH is adjusted by addition of an aqueous alkaline solution to the pH which the aqueous solution comprising sulfonated arylphosphine has to have for the subsequent catalyst preformation or hydroformylation reaction. In general, the pH in the subsequent hydroformylation reaction is in a range from 5 to 6.5. As aqueous alkaline solutions, use is made of an alkali metal hydroxide or alkaline earth metal hydroxide or alkali metal carbonate or alkaline earth metal carbonate solution, preferably an aqueous sodium hydroxide solution.

The gas treatment of the solutions is carried out at a temperature of from 0° C. to 100° C. Particular preference is given to a temperature range from 10° C. to 40° C.

In this procedure, salts are additionally formed in the aqueous solution comprising sulfonated arylphosphines to be used for the hydroformylation reaction as a result of the addition of acid and subsequently alkali. These salts, for example $Na_2SO_4$, can either remain in the solution or, according to the work-up process of EP-A-0 632 047, be removed by extraction with the solution of a water-insoluble amine, for example triisooctylamine, in a water-insoluble solvent and subsequent reextraction with the solution of an inorganic base in water. Suitable bases are hydroxides of the alkali metals and alkaline earth metals, in particular alkali metal hydroxide, ammonia and also the alkali metal carbonates.

The amount of inert gas per kg of aqueous solution comprising the sulfonated arylphosphine and the time of treatment with the gas depend on the geometry of the gas treatment apparatus. In general, the conditions and the geometry are to be selected so that the aqueous solution comprising the sulfonated arylphosphine is largely freed of $SO_2$ present (at least 90%). In a continuous gas treatment, for example in a packed column, a mean gas treatment time of from 2 to 100 minutes, preferably from 2 to 20 minutes, is suitable. A total amount in the range from 5 to 500 l of inert gas, preferably from 10 l to 200 l, particularly preferably from 20 to 100 l, is required per kg of aqueous solution comprising the sulfonated arylphosphine in a continuous gas treatment apparatus. In the case of a gas treatment carried out batchwise, from 5 l to 1000 l of inert gas per kg of aqueous solution are used. Here, the amount of inert gas is preferably from 10 l to 200 l and particularly preferably from 20 l to 100 l per kg of aqueous solution comprising the sulfonated arylphosphine. In the gas treatment carried out batchwise, the gas treatment time is generally from 1 to 100 hours, preferably from 5 to 50 hours and particularly preferably from 10 to 20 hours.

Starting compounds for the sulfonation according to the various embodiments of the process of the invention are arylphosphines. For the purposes of the present invention, this general designation includes monophosphines, diphosphines, oligophosphines and polyphosphines which contain at least one aromatic radical. Aromatic radicals also include those which are linked to one another by single C—C bonds, e.g. biphenyl, but also, in particular, fused ring systems such as naphthyl or indenyl radicals.

The aromatic radicals may additionally bear one or more substituents such as chlorine, fluorine, alkyl groups having from 1 to 10 carbon atoms, alkoxy groups having from 1 to 10 carbon atoms and nitro groups. Examples of monophosphines which can be sulfonated by the process of the invention are dimethylphenylphosphine, methyldiphenylphosphine and triphenylphosphine. Examples of diphosphines are 2,2'-bis(diphenlyphosphinomethyl)biphenyl and 2,2'-bis(diphenlyphosphinomethyl)binaphthyl. The arylphosphines suitable for the purposes of the invention also include compounds of trivalent phosphorus in which the phosphorus atom is part of a ring system. Examples of this class of compounds are phosphabenzene substituted by aromatic radicals and aryl- and/or alkyl-substituted phosphols. Examples of such compounds are described in J. Mol. Cat. A, 116 (1997), pp. 3–26.

As inert gases for the gas treatment of the diluted sulfonation mixture or the acidified aqueous solution comprising the sulfonated arylphosphines, it is possible to use all gases which do not react chemically with the added acid or the dissolved arylphosphines. Examples of inert gases are nitrogen, the noble gases helium, neon, argon, xenon and krypton, carbon dioxide, carbon monoxide and hydrogen, with nitrogen and the cheaper noble gases being preferred.

The various embodiments of the process of the invention are particularly suitable for treating aqueous TPPTS solutions.

The $SO_2$-laden inert gas stream cannot be discharged into the atmosphere without treatment. It is therefore passed through a scrubbing solution in which the $SO_2$ is absorbed. This scrubbing solution can be a basic liquid, for example a sodium carbonate solution or an NaOH solution. However, waste sulfuric acid can also be used as scrubbing liquid.

The invention will be illustrated below for those skilled in the art by means of the following examples, without implying a restriction to the concrete embodiments presented.

EXAMPLE 1

Degassing of a diluted sulfonation mixture from the sulfonation of triphenylphosphine (TPPTS content about 3%, Sulfuric Acid About 25%)

962.3 g of the above, diluted sulfonation mixture were placed in a 106 cm long bubble column having an internal diameter of 4 cm and treated at room temperature with nitrogen at a flow rate of 20 l/h.

The gas stream leaving the bubble column was passed through a wash bottle containing 200 g of a 2.7% strength sodium carbonate solution. Samples were taken from this wash bottle and analyzed for sulfite and sulfate by means of ion chromatography. It was found that all the sulfate in the wash bottle originated from the oxidation of sulfate since even after a very long gas treatment time the amount of sulfate does not increase further. This would, however, have to occur if sulfuric acid were to be carried as aerosol in the inert gas from the diluted sulfonation mixture. These specific measurement results are shown in the following table.

TABLE 1

Degassing of the diluted sulfonation mixture using nitrogen as a function of the degassing time.

| Gas treatment Time min. | Waste gas Liters | Sulfite % | Sulfate % | % of hydrolysis mixture | | |
|---|---|---|---|---|---|---|
| | | | | $SO_3^{2-}$ | $SO_4^{2-}$ | Total $SO_3^{2-}$ + $SO_4^{2-}$ |
| 0 | 0.2 | — | 0.01 | — | 0.002 | 0.002 |
| 10 | 3.4 | 0.07 | 0.01 | 0.014 | 0.002 | 0.016 |
| 20 | 6.3 | 0.06 | 0.08 | 0.012 | 0.016 | 0.028 |
| 30 | 8.9 | 0.1 | 0.08 | 0.02 | 0.016 | 0.036 |
| 60 | 21 | 0.21 | 0.1 | 0.043 | 0.02 | 0.065 |
| 90 | 29.5 | 0.2 | 0.17 | 0.041 | 0.034 | 0.075 |
| 120 | 42 | 0.25 | 0.16 | 0.051 | 0.032 | 0.083 |
| 990 | 451.2 | 0.32 | *0.13 | 0.064 | 0.026 | 0.09 |

Work-up according to the teachings of EP-A-0 632 047 gave a 15% strength TPPTS solution. The sulfite content of this solution was below the detection limit of 0.01% by weight, measured by the method of ion chromotography.

EXAMPLE 2

Comparative Example

Example 1 was repeated, except that a gas treatment of the diluted sulfonation mixture was not carried out. Work-up in accordance with EP-A-0 632 047 gave a 15% strength TPPTS solution on which a sulfite content of 0.20% weight was measured.

EXAMPLE 3

The TPPTS solution from Example 1 was used in a continuous hydroformylation using propene as olefin, 50 bar of synthesis gas, 300 ppm of rhodium and 300 mmol of TPPTS/kg. At a reaction temperature of 134° C., a sulfur content of 1.7 ppm was found in the butanal collected after a reaction time of 211 hours.

EXAMPLE 4

Comparative Example

The TPPTS solution from Example 2 was used in a continuous hydroformylation as described in Example 3. After a reaction time of 230 hours, a sulfur content of 6.5 ppm was found in the butanal formed.

EXAMPLE 5

Continuous Degassing, See FIG. 1

200 l/h of the hydrolysis mixture having a comparable composition to that in Example 1 were introduced at the top into a desorber column A having a length of 8 m and an internal diameter of 10 cm and packed with 15 mm Pall rings. 8.8 m³/h of nitrogen were introduced into the column in countercurrent from below. After establishment of equilibrium, degassing of 92% of the sulfur dioxide originally present was found. Work-up in accordance with EP-A-0 632 047 gave a 15% strength TPPTS solution on which a sulfite content of 0.02% by weight was measured.

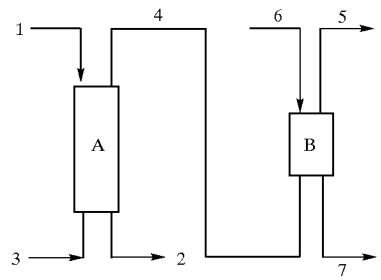

1 Inlet for hydrolysis mixture
2 Outlet for hydrolysis mixture
3 Inlet for nitrogen
4 Outlet for nitrogen laden with sulfur dioxide
5 Purified waste gas
6 Inlet for scrubbing solution
7 Outlet for scrubbing solution laden with sulfur dioxide

EXAMPLE 6

Degassing of a TPPTS solution (solution of tris(m-sulfophenyl)phosphine trisodium salt) at a pH of 0 (TPPTS content about 27% by weight, sulfite content 0.338% by weight).

2500 g of a TPPTS solution, sulfonated by the method known from DE-A-26 27 454 and worked up by the method known from EP-A-0 632 047, containing 8.46 g of $SO_3^{2-}$ were admixed with 314 g of $H_2SO_4$ (65% strength) and treated intensively with nitrogen gas in a 4 l three-necked flask with frit attachment and frit filter. The gas treatment was carried out at 20° C. using nitrogen at a flow rate of 20 l/h.

The gas stream leaving the flask was passed through a wash bottle containing 400 g of a sodium carbonate/sodium hydrogen carbonate solution (0.4 mol of $Na_2CO_3$, 0.15 mol of $NaHCO_3$). Samples were taken from this wash bottle and analyzed for sulfite and sulfate by means of ion chromatography, with all sulfite being converted into sulfate by oxidation. It was found that the total sulfate content in the sodium carbonate/sodium hydrogen carbonate solution originates from the oxidation of sulfite since even after a very long gas treatment time the amount of sulfate did not increase further. This would, however, have had to occur if sulfuric acid had been carried as aerosol in the inert gas from the acidified aqueous TPPTS solution. The specific measurement results are shown in the following table. The measured values in the second-last column represent the sulfate values found by analysis of the sodium carbonate/sodium hydrogen carbonate solution (third-last column) and calculated as sulfite.

TABLE 2

Degassing of an aqueous TPPTS solution using nitrogen as a function of the degassing time

| Running time [h] | Starting TPPTS solution [g] | $Na_2CO_3$/ $NaHCO_3$ Solution [g] | $SO_4^{2-}$ in the $Na_2CO_3$/ $NaHCO_3$ solution [% by wt.] | $SO_3^{2-}$ carried from TPPTS solution [g] | Degree of degassing [%] |
| --- | --- | --- | --- | --- | --- |
| 0 | 2814 | 400.4 | <0.01 | <0.03 | 0 |
| 1 | 2809 | 399.2 | 1.24 | 4.13 | 48.8 |
| 3 | 2804 | 398.0 | 2.05 | 6.82 | 80.6 |
| 24 | 2799 | 397.8 | 2.4 | 7.96 | 94.1 |

(Degree of degassing means: $SO_3^{2-}$ in gram carried from the TPPTS solution, based on the amount in gram of $SO_3^{2-}$ in the TPPTS solution prior to degassing).

2742 g of the gas-treated TPPTS solution were stirred at 32° C. with 5928 g of a mixture of triisooctyl-amine/toluene having a triisooctylamine content of 28% by weight in a 10 l three-necked flask for 1 hour. After separating off the organic phase, the latter was reextracted with an aqueous 10% strength sodium hydroxide solution. The subsequent reextraction served to separate off the sulfate introduced by acidification with sulfuric acid. The three reextraction steps are shown in the following table.

TABLE 3

Reextraction of the organic phase obtained from extraction of the acidified and gas-treated, aqueous TPPTS solution

|  | 1st step | 2nd step | 3rd step |
| --- | --- | --- | --- |
| Adjustment to pH = | 3.54 | 8.00 | 12.90 |
| Consumption of NaOH [g] | 405 | 1701 | 160 |
| Final weight of TPPTS solution [g] | 166.0 | 2574.8 | 166.0 |
| $P^3$ content [mmol] | 0 | 1296.3 | 3.2 |
| Yield [%] | 0 | 97.2 | 0.2 |

As shown by Table 3, in a pH range of up to 3.54, the sulfate goes over from the organic phase into the aqueous phase, while in the reextraction in the pH range from 3.54 to 8.00, the desired TPPTS goes over from the organic phase into the aqueous phase.

EXAMPLE 7

Degassing of a TPPTS solution at a pH of 1
(TPPTS content about 27% by weight, sulfite content 0.34% by weight).

2500 g of a TPPTS solution as used in Example 6 and containing 8.5 g of $SO_3^{2-}$ were admixed with 18 g of $H_2SO_4$ (65% strength) and intensively treated with nitrogen gas in a 4 l three-necked flask with frit attachment and frit filter. The gas treatment was carried out at 20° C. using nitrogen at a flow rate of 20 l/h.

The gas stream leaving the three-necked flask was passed through a wash bottle containing 400 g of a sodium carbonate/sodium hydrogen carbonate solution (0.4 mol of $Na_2CO_3$, 0.15 mol of $NaHCO_3$). Samples were taken from this wash bottle and analyzed for sulfite and sulfate by means of ion chromatography, with all sulfite being converted into sulfate by oxidation. It was found that the total sulfate content in the sodium carbonate/sodium hydrogen carbonate solution originates from the oxidation of sulfite since even after a very long gas treatment time the amount of sulfate did not increase further. This would, however, have had to occur if sulfuric acid had been entrained as aerosol in the inert gas stream from the acidified, aqueous TPPTS solution. The specific measurement results are shown in the following table.

TABLE 4

Degassing of an aqueous TPPTS solution set to a pH of 1 as a function of the degassing time

| Running time [h] | Starting TPPTS solution [g] | $Na_2CO_3$/ $NaHCO_3$ Solution [g] | $SO_4^{2-}$ in the $Na_2CO_3$/ $NaHCO_3$ solution [%] | $SO_3^{2-}$ carried from TPPTS solution [g] | Degree of degassing [%] |
| --- | --- | --- | --- | --- | --- |
| 0 | 2518 | 399 | <0.01 | <0.03 | 0 |
| 1 | 2516 | 397.8 | 0.16 | 0.53 | 6.3 |
| 3 | 2511 | 396.6 | 1.39 | 4.61 | 54.2 |
| 24 | 2509 | 387.8 | 2.3 | 7.48 | 88.1 |

The gas-treated TPPTS solution was not worked up by means of extraction and reextraction as in Example 6, but was brought to a pH of 6.5 by addition of a 10% strength NaOH solution. The $Na_2SO_4$ formed was left in the solution.

EXAMPLE 8

Degassing of a TPPTS solution at a pH of 2
(TPPTS content about 27% by weight, sulfite content 0.34% by weight).

2500 g of a TPPTS solution as used in Example 6 and containing 8.5 g of $SO_3^{2-}$ were admixed with 4.72 g of $H_2SO_4$ (65% strength) and intensively treated with nitrogen gas in a 4 l three-necked flask with frit attachment and frit filter. The gas treatment was carried out at 20° C. using nitrogen at a flow rate of 20 l/h.

The gas stream leaving the three-necked flask was passed through a wash bottle containing 400 g of a sodium carbonate/sodium hydrogen carbonate solution (0.4 mol of $Na_2CO_3$, 0.15 mol of $NaHCO_3$). Samples were taken from this wash bottle and analyzed for sulfite and sulfate by means of ion chromatography, with all sulfite being converted into sulfate by oxidation. It was found that the total sulfate content in the sodium carbonate/sodium hydrogen carbonate solution originates from the oxidation of sulfite since even after a very long gas treatment time the amount of sulfate did not increase further. This would, however, have had to occur if sulfuric acid had been entrained as aerosol in the inert gas stream from the acidified, aqueous TPPTS solution. The specific measurement results are shown in the following table.

TABLE 5

Degassing of an aqueous TPPTS solution set to a pH of 2 as a function of the degassing time

| Running time [h] | Starting TPPTS solution [g] | $Na_2CO_3$/ $NaHCO_3$ solution [g] | $SO_4^{2-}$ in the $Na_2CO_3$/ $NaHCO_3$ solution [%] | $SO_3^{2-}$ carried from TPPTS solution [g] | Degree of degassing [%] |
|---|---|---|---|---|---|
| 0 | 2500 | 402.9 | <0.01 | <0.03 | 0 |
| 1 | 2498 | 401.8 | 0.12 | 0.40 | 4.8 |
| 3 | 2494 | 399.8 | 0.47 | 1.58 | 18.8 |
| 24 | 2491 | 388.7 | 1.76 | 5.85 | 69.6 |

The gas-treated TPPTS solution was not worked up by means of extraction and reextraction as in Example 6, but was brought to a pH of 6.5 by addition of a 10% strength NaOH solution. The $Na_2SO_4$ formed was left in the solution.

As can be seen from Tables 2, 4 and 5, a rising degree of degassing is observed with decreasing pH.

EXAMPLE 9

Hydroformylation Using the TPPTS Solution Treated as Described in Example 6

A TPPTS solution treated as described in Example 6 (reextraction after the degassing step) and having a TPPTS content of 300 mmol/kg was used in a continuous hydroformylation using propene as olefin at a synthesis gas pressure of 50 bar. The rhodium concentration of the aqueous catalyst solution was 300 ppm of rhodium. At a reaction temperature of 134° C., a sulfur content of 1.6 ppm was found in the butanal obtained after a reaction time of 211 hours.

EXAMPLE 10

Hydroformylation Using the TPPTS Solution Treated as Described in Example 8

A TPPTS solution treated as described in Example 8 (no reextraction after the degassing step) and having a TPPTS content of 300 mmol/kg was used in a continuous hydroformylation using propene as olefin at a synthesis gas pressure of 50 bar. The rhodium concentration of the aqueous catalyst solution was 300 ppm of rhodium. At a reaction temperature of 134° C., a sulfur content of 2.5 ppm was found in the butanal obtained after a reaction time of 211 hours.

EXAMPLE 11

Comparative Example using a TPPTS solution which has not been degassed

The untreated TPPTS solution from Example 6 having a sulfite content of 0.38% by weight and a TPPTS content of 300 mmol/kg was, without carrying out the acidification and gas treatment according to the invention, used in a continuous hydroformylation using propene as olefin at a synthesis gas pressure of 50 bar. The rhodium content was 300 ppm, based on the aqueous solution. After a reaction time of 230 hours, a sulfur content of 9.8 ppm was found in the butanal obtained.

As comparison of Examples 9 and 10 with Comparative Example 11 demonstrates the use of an aqueous TPPTS solution treated according to the invention in the hydroformylation reaction gives aldehydes which have a significantly lower sulfur content. The use of such aldehydes in the preparation of alcohols in downstream hydrogenation processes is particularly advantageous since poisoning of the hydrogenation catalysts by sulfur compounds is avoided. Furthermore, aldehydes having a low sulfur content have a high stability against trimerization and condensation reactions during storage.

What is claimed is:

1. A process for preparing solutions of sulfonated arylphosphines comprising reacting arylphosphines with oleum to form a sulfonation mixture, diluting the sulfonation mixture with water, extrating the diluted sulfonation mixture with a solution of a water-insoluble amine in a water-insoluble organic solvent, reacting the resulting water-immiscible organic phase with a solution of an inorganic base in water, adjusting the resulting aqueous solution of sulfonated arylphosphines of pH of up to 3 by addition of an acid, and passing an inert gas stream through the aqueous solution comprising sulfonated arylphosphines until sulfur dioxide is no longer liberated from the aqueous solution of sulfonated arylphosphines.

2. The process of claim 1, wherein the arylphosphines are selected from the group consisting of monophosphines, diphosphines, oligophosphines and polyphosphines containing at least one aromatic ring.

3. The process of claim 1, wherein the monophosphine is selected from the group consisting of methyldiphenylphosphine and triphenylphosphine.

4. The process of claim 1, wherein the aqueous solution comprising sulfonated arylphosphines is adjusted to a pH of 0–2 by addition of an acid.

5. The process of claim 1, wherein the aqueous solution comprising sulfonated arylphosphines is admixed with inorganic or organic acids to adjust the pH to 3.

6. The process of claim 5, wherein the acid is selected from the group consisting of sulfuric acid, phosphoric acid, nitric acid, hydrochloric acid, formic acid and acetic acid.

7. The process of claim 1, therein an inert gas stream is passed continuously or discontinuously through the aqueous solution comprising sulfonated arylphosphines.

8. The process of claim 1, wherein the inert gas is at least one member of the group consisting of nitrogen, helium, neon, argon, xenon and krypton, carbon dioxide, carbon monoxide and hydrogen.

9. The process of claim 1, wherein the inert gas treatment is carried out for 2 to 100 minutes and the amount of an insert gas per kg of aqueous solution comprising the sulfonated arylphosphine is 5 to 500 liters of inert gas, the sulfite content in the aqueous solution comprising sulfonated arylphosphines being <0.1% by weight.

10. The process of claim 1, wherein the inert gas treatment is carried out for 1 to 100 hours and the amount of inert gas per kg of aqueous solution comprising the sulfonated arylphosphine is 5 to 1000 liter of inert gas, the sulfite content in the aqueous solution comprising sulfonated arylphosphines being <0.1% by weight.

11. The process of claim 1, wherein the inert gas stream laden with sulfur dioxide is passed through a scrubbing solution into which sulfur dioxide is absorbed, with the scrubbing solution being a basic liquid.

* * * * *